(12) United States Patent
Watanabe et al.

(10) Patent No.: US 6,346,646 B1
(45) Date of Patent: Feb. 12, 2002

(54) PROCESS FOR PRODUCING METHACROLEIN AND METHACRYLIC ACID

(75) Inventors: Seigo Watanabe; Motomu Oh-Kita, both of Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/463,385

(22) PCT Filed: Nov. 25, 1998

(86) PCT No.: PCT/JP98/05295

§ 371 Date: Jan. 27, 2000

§ 102(e) Date: Jan. 27, 2000

(87) PCT Pub. No.: WO99/26912

PCT Pub. Date: Jun. 3, 1999

(30) Foreign Application Priority Data

Nov. 25, 1997 (JP) .............................................. 9-338258

(51) Int. Cl.[7] .............................................. C07C 51/25
(52) U.S. Cl. .......................... 562/534; 502/38; 568/477; 568/478; 568/479; 568/480
(58) Field of Search .......................... 562/534; 568/477, 568/478, 479, 480; 502/38

(56) References Cited

U.S. PATENT DOCUMENTS 4,186,152 A * 1/1980 Yamamoto et al.

FOREIGN PATENT DOCUMENTS

| GB | 2029719 A | * | 3/1980 |
| JP | 61-33234 A | | 2/1986 |
| JP | 63-137755 A | | 6/1988 |
| JP | 63-145249 A | | 6/1988 |
| JP | 4-279542 A | | 10/1992 |
| WO | 99/26915 | | 6/1999 |

OTHER PUBLICATIONS

Chemical Abstracts, vol. 87, No. 10, Sep. 5, 1977, "Purification of (meth)acrylic acids and their esters", 87:68862j; p. 15, col. r.

* cited by examiner

Primary Examiner—Paul J. Killos
Assistant Examiner—Robert W. Deemie
(74) Attorney, Agent, or Firm—Oblon, Spivak, McClelland, Maier & Neustadt, P.C.

(57) ABSTRACT

A process for producing methacrolein and methacrylic acid by catalytically oxidizing isobutylene or tertiary butanol in the presence of a catalyst comprising a compound oxide containing molybdenum, bismuth and iron as the essential components, wherein a catalytic oxidation reaction is started at a temperature of (T−3)° C. or lower wherein T° C. is defined as the boundary temperature of activation energy of a reaction for obtaining methacrolein and methacrylic acid from isobutylene using said catalyst, the reaction is continued while the reaction temperature is increased as the activity of the catalyst decreases, and an activation treatment is conducted for the catalyst at least once before the reaction temperature exceeds the boundary temperature of activation energy.

7 Claims, No Drawings

PROCESS FOR PRODUCING METHACROLEIN AND METHACRYLIC ACID

TECHNICAL FIELD

The present invention relates to a process for producing methacrolein and methacrylic acid, particularly a process for producing methacrolein and methacrylic acid by subjecting isobutylene or tertiary butanol to gas-phase catalytic oxidation with molecular oxygen in the presence of a catalyst.

BACKGROUND ART

A process for producing methacrolein and methacrylic acid by catalytically oxidizing isobutylene or tertiary butanol in the presence of a catalyst composed of a compound oxide containing molybdenum, bismuth and iron as the essential components, is well known and actually in wide use. In this process, the reaction is conducted at a temperature of 300 to 400° C. with the catalyst being used in the form of a fixed bed.

The catalyst used in such a gas-phase catalytic oxidation reaction is used for a relatively long period of time. Meanwhile, the activity of catalyst generally decreases with the lapse of time. In JP-B-5-29502 is disclosed a method for regeneration of catalyst, which comprises regenerating a multi-component (Mo—Bi—Fe) oxide catalyst whose catalytic activity has decreased owing to the use in reaction, in an atmosphere composed substantially of air, at a temperature of 380 to 540° C.; and in JP-B-5-70503 is disclosed a method for regeneration of catalyst, which comprises regenerating a catalyst (similar to the above) whose catalytic activity has decreased, in a stream of an oxidizing gas composed of 5–99.9% by volume of oxygen, 0.1–95% by volume of steam and an inert gas, at a temperature of 300 to 500° C.

The investigation by the present inventors, however, indicated that in the regenerations of activity-deteriorated catalyst as mentioned in the above publications, the catalyst performance is once recovered, by the regeneration, to a level of fresh catalyst but the catalyst after regeneration shows rapid decrease in activity. Thus, the above-mentioned regenerations are not fully satisfactory from the standpoint of industrial application.

Hence, the present invention is intended to provide a process for producing methacrolein and methacrylic acid by subjecting isobutylene or tertiary butanol to gas-phase catalytic oxidation with molecular oxygen in the presence of a catalyst, in which process the catalyst can be used over a long period of time.

DISCLOSURE OF THE INVENTION

The present invention is a process for producing methacrolein and methacrylic acid by catalytically oxidizing isobutylene or tertiary butanol in the presence of a catalyst comprising a compound oxide containing molybdenum, bismuth and iron as essential components, wherein a catalytic oxidation reaction is started at a temperature of (T−3)° C. or lower wherein T° C. is defined as a boundary temperature of activation energy of a reaction for obtaining methacrolein and methacrylic acid from isobutylene using said catalyst (hereinafter referred to as the boundary temperature of activation energy), the reaction is continued while a reaction temperature is increased as an activity of the catalyst decreases, and an activation treatment is conducted for the catalyst at least once before the reaction temperature exceeds the boundary temperature of activation energy.

BEST MODE FOR CARRYING OUT THE INVENTION

The catalyst used in the present invention comprises a compound oxide containing molybdenum, bismuth and iron as the essential components, and there is no particular restriction as to other components. This catalyst can be produced by a known method described in JP-A-53-19188, JP-A-54-66610, JP-A-55-359, JP-A-55-19227, JP-A-56-95135, JP-A-60-28824 and the like.

It is known that in gas-phase catalytic reactions using a solid catalyst, the activation energy of intended reaction often differs between low and high reaction temperature ranges which are divided by a certain boundary temperature. In, for example, JOURNAL OF CATALYSTS, Vol. 41, pp. 134–139 (1976) it is reported that different activation energies such as mentioned above exist in the catalytic oxidation reaction of 1-butene in the presence of a catalyst composed of a molybdenum- and bismuth-containing compound oxide. Such a phenomenon is seen because the rate-determining step of reaction differs by the level of reaction temperature, and is explained in detail in Catalysts Course, Vol. 1, Paragraph 4, compiled by the Japan Society of Catalyst and published by Kodansha. According to one theory, the reaction of reactant molecules on catalyst active sites is a rate-determining step in a low reaction temperature range and the diffusion of reactant molecules into catalyst active sites is a rate-determining step in a high reaction temperature range.

The present inventors made an analysis on the activation energy of a reaction in which methacrolein and methacrylic acid are produced by subjecting isobutylene to catalytic oxidation in the presence of a catalyst composed of a compound oxide containing molybdenum, bismuth and iron as the essential components and, as a result, confirmed that the activation energy of the reaction was different in a low reaction temperature range and in a high reaction temperature range.

In the present invention, the boundary temperature of activation energy is determined as follows.

First, in case isobutylene is used as the raw material of the reaction, a catalyst is packed in a reaction tube provided with a heat medium bath; the temperature of the heat medium bath is varied in the range of 315 to 375° C. at intervals of 2 to 5° C.; the conversion of isobutylene at each temperature is determined. The conversion is determined from the following formula:

$$\text{Conversion (\%) of raw material} = (A/B) \times 100 \quad (1)$$

wherein A is the moles of the raw material reacted, and B is the moles of the raw material fed.

Next, the rate constant of the reaction is determined from the following formula:

$$K = (SV) \times (1/\rho) \times \ln[100/(100-X)] \quad (2)$$

wherein K is the rate constant of the reaction, SV is the space velocity of reactant gas, $\rho$ is the packing density of the catalyst, and X is the conversion (%) of raw material.

Next, $1/T$ is taken as axis of abscissa and $\ln K$ is taken as axis of ordinate; data are plotted on the graph; two approximate straight lines are drawn; and the inclinations of the two lines are determined. Here, $1/T$ is the reciprocal of the heat medium bath temperature (absolute temperature), and $\ln K$ is the natural logarithm of the rate constant of the reaction. The approximate straight lines can be determined by an ordinary method such as method of least squares or the like.

The absolute value of the obtained inclination of each approximate straight line is multiplied by gas constant. The resulting product is an intended activation energy. The reciprocal of the abscissa of the intersection point of the two approximate straight lines is an intended boundary temperature of activation energy.

When tertiary butanol is used as the raw material of reaction in place of isobutylene, tertiary butanol is decomposed rapidly into isobutylene and water on a catalyst containing molybdenum, bismuth and iron as the essential components. That is, the reaction mechanism when tertiary butanol is used as the raw material of reaction, may be considered to be substantially the same as in the oxidation reaction of isobutylene. Hence, the boundary temperature of activation energy in a reaction using isobutylene as the raw material of reaction can be utilized as it is, also in a reaction using tertiary butanol as the raw material.

In industrial use of catalyst, various measures are generally taken to extend the life of packed catalyst as much as possible. It is conducted, for example, to increase, with the degradation of the packed catalyst, the reaction temperature gradually up to an allowable limit of process to maintain an intended conversion.

The present inventors have found that in producing methacrolein and methacrylic acid by catalytically oxidizing isobutylene or tertiary butanol in the presence of a catalyst comprising a compound oxide containing molybdenum, bismuth and iron as the essential components, the life of the catalyst can be extended significantly by starting the catalytic oxidation reaction at a temperature of $(T-3)°$ C. or lower wherein $T°$ C. is defined as the boundary temperature of activation energy, continuing the reaction while the reaction temperature is increased as the activity of the catalyst decreases, and conducting an activation treatment for the catalyst at least once before the reaction temperature exceeds said boundary temperature.

Decrease in activity of catalyst is caused by various reasons such as reduction of catalyst components, sublimation or vaporization of catalyst components, change of crystalline phase in catalyst structure and the like. To reactivate a catalyst whose activity has decreased owing to these reasons, known catalyst regeneration methods such as those mentioned in the above Background Art can be utilized. However, a catalyst regeneration method is preferred wherein a catalyst to be reactivated is kept at a temperature of not less than 300° C. but less than 550° C. and contacted with a gas substantially composed of air for at least one hour. The treatment for catalyst activation may be conducted by taking out the catalyst from the reactor; however, treatment in a state in which the catalyst is packed in the reactor, is advantageous industrially because it allows easy operation.

When the above activation treatment is conducted for a catalyst which has been used up to a reaction temperature higher than the boundary temperature of activation energy, however, the catalyst regains its activity once; however, in its subsequent use, the activity decreases rapidly and the effect of catalyst life extension is low. In contrast, when the above activation treatment is conducted, as in the present process, for a catalyst which has been used only at a temperature lower than the boundary temperature of activation energy, not only the catalyst regains its activity but also the rate of activity decrease in use of the treated catalyst is the same as that of fresh catalyst.

In the present invention, the temperature at which the reaction is started, must be $(T-3)°$ C. or lower when $T°$ C. is defined as the boundary temperature of activation energy of the reaction. When the temperature is higher than $(T-3)°$ C., the time period from the reaction start to the activation treatment of catalyst is too short, which is disadvantageous industrially. The temperature of reaction start can be controlled depending upon the activity or packing amount of catalyst, the composition or rate of reactant gas, the pressure of reaction, the conversion of raw material, etc.

In the present invention, there is no particular restriction as to the times of the activation treatment, and the activation treatment can be repeated whenever there arises decrease in catalyst activity. As long as the selectivity of intended product is in an allowable range, the reaction can be continued while the activation treatment is repeated, and this practice is advantageous industrially because the catalyst can be used over a long period of time.

In the present invention, the activation treatment for catalyst must be conducted at least once before the reaction temperature exceeds the boundary temperature of activation energy. After this activation treatment, however, there is no particular restriction as to the operation of reaction. After the activation treatment, it is possible, for example, to continue the reaction at a temperature higher than the boundary temperature of activation energy or to conduct an activation treatment for a catalyst which has been used up to such a temperature.

The present invention is hereinafter described in further detail by reference to Examples. In the Examples, "parts" refer to parts by weight. Analysis of reaction products was made by gas chromatography. The conversion of isobutylene or tertiary butanol as raw material of reaction is as defined in the above formula (1). The selectivity of methacrolein or methacrylic acid produced is defined as follows.

$$\text{Selectivity (\%) of methacrolein}=(C/A)\times 100 \tag{3}$$

wherein A is the moles of raw material reacted, and C is the moles of methacrolein formed.

$$\text{Selectivity (\%) of methacrylic acid}=(D/A)\times 100 \tag{4}$$

wherein A is the moles of raw material reacted, and D is the moles of methacrylic acid formed.

REFERENCE EXAMPLE 3,000 parts of ammonium paramolybdate was dissolved in 6,000 parts of water. Thereto was added 330.2 parts of antimony trioxide with stirring. The mixture was heated to 50° C. (solution A). Separately, in 5,500 parts of water were dissolved 858.1 parts of iron (III) nitrate, 3,296.8 parts of cobalt nitrate, 84.3 parts of zinc nitrate and 110.4 parts of cesium nitrate. Thereto was added a solution of 150 parts of 60% nitric acid and 686.9 parts of bismuth nitrate dissolved in 300 parts of water. The mixture was heated to 30° C. (solution B).

The solution A and the solution B were mixed with stirring to obtain a slurry. The slurry was aged at 90° C. for 2 hours, thereafter heated to 103° C. and concentrated for 1 hour, and then dried by the use of a spray dryer to obtain a dry powder. The dry powder was calcined at 300° C. for 4 hours to obtain a catalyst precursor powder having the following composition.

$$Mo_{12}Bi_1Fe_{1.5}Co_8Zn_{0.2}Cs_{0.4}Sb_{0.8}O_x$$

wherein Mo, Bi, Fe, Co, Zn, Cs, Sb and O refer to molybdenum, bismuth, iron, cobalt, zinc, cesium, antimony and oxygen, respectively; the number suffixed after each element symbol is the atomic ratio of the element; and x is the atomic ratio of oxygen necessary for satisfying the valences of elements other than oxygen.

3,920 parts of the catalyst precursor powder was thoroughly mixed with 80 parts of a graphite powder. The mixture was molded into a column of 4 mm in outer diameter and 4 mm in height. The molded material was calcined at 510° C. for 2 hours to obtain a catalyst.

2,000 g of the catalyst was packed in a stainless steel-made reaction tube of 27.5 mm in inner diameter and 4 m in height, provided with a heat medium bath at the outer surface. Then, a raw material mixed gas composed of 5% by volume of isobutylene, 12% by volume of oxygen, 10% by volume of steam and 73% by volume of nitrogen was passed through the catalyst layer at a contact time of 3.5 seconds. During the passing, the temperature of the heat medium bath was varied in a range of 315 to 375° C. at intervals of 2 to 5° C. The conversions of isobutylene at various temperatures were determined and, using the conversions, activation energies were calculated. As a result, the boundary temperature of activation energy was 335° C., and the activation energy in a temperature range lower than the boundary temperature was 102 kJ/mole and the activation energy in a temperature range higher than the boundary temperature was 35 kJ/mole.

Example 1

2,000 g of the catalyst obtained in Reference Example was packed in the same reaction tube as used in Reference Example. Then, a raw material mixed gas composed of 5% by volume of isobutylene, 12% by volume of oxygen, 10% by volume of steam and 73% by volume of nitrogen was passed through the catalyst layer at a contact time of 4.5 seconds with the temperature of the heat medium bath being kept at 325° C. The reaction products were analyzed; as a result, the conversion of isobutylene was 95.5%, the selectivity of methacrolein was 87.7% and the selectivity of methacrylic acid was 5.3%. This reaction was conducted continuously in the following manner: That is, the temperature of the heat medium bath was controlled when the conversion changed owing to the change in catalytic activity, whereby the conversion was kept substantially constant. When the reaction was continued until the temperature of the heat medium bath became 330° C., the time period of continuous operation was 9,600 hours. At that time, the conversion of isobutylene was 95.4%, the selectivity of methacrolein was 87.7% and the selectivity of methacrylic acid was 5.3%.

The reaction was stopped; air instead of the raw material mixed gas was passed through the catalyst layer at a contact time of 4.0 seconds; the temperature of the heat medium bath was increased to 380° C. and kept at the same temperature for 24 hours; thereby, a first catalyst activation treatment was conducted. Thereafter, the heat medium bath was cooled to 323° C. and the same raw material mixed gas as used above was passed through the catalyst layer at a contact time of 4.5 seconds to restart the reaction. The reaction products were analyzed; as a result, the conversion of isobutylene was 95.5%, the selectivity of methacrolein was 87.7% and the selectivity of methacrylic acid was 5.3%. This reaction was conducted continuously in the same manner as above. When the reaction was continued until the temperature of the heat medium bath became 330° C., the time period of continuous operation after the activation treatment was 8,400 hours. At that time, the conversion of isobutylene was 95.7%, the selectivity of methacrolein was 87.5% and the selectivity of methacrylic acid was 5.3%.

The reaction was stopped again; air was passed through the catalyst layer at a contact time of 4.0 seconds; the temperature of the heat medium bath was increased to 380° C. and kept at the same temperature for 24 hours; thereby, a second catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of isobutylene was 95.3%, the selectivity of methacrolein was 87.7% and the selectivity of methacrylic acid was 5.3%. This reaction was conducted continuously in the same manner as above. When the reaction was continued until the temperature of the heat medium bath became 330° C., the time period of continuous operation after the activation treatment was 8,400 hours. At that time, the conversion of isobutylene was 95.5%, the selectivity of methacrolein was 87.5% and the selectivity of methacrylic acid was 5.3%.

The reaction was stopped once again; air was passed through the catalyst layer at a contact time of 4.0 seconds; the temperature of the heat medium bath was increased to 380° C. and kept at the same temperature for 24 hours; thereby, a third catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of isobutylene was 95.2%, the selectivity of methacrolein was 87.7% and the selectivity of methacrylic acid was 5.3%. This reaction was conducted continuously in the same manner as above. When the reaction was continued until the temperature of the heat medium bath became 330° C., the time period of continuous operation after the activation treatment was 8,400 hours. At that time, the conversion of isobutylene was 95.4%, the selectivity of methacrolein was 87.5% and the selectivity of methacrylic acid was 5.3%.

Comparative Example 1

2,000 g of the catalyst obtained in Reference Example was packed in the same reaction tube as used in Reference Example. Then, a raw material mixed gas composed of 5% by volume of isobutylene, 12% by volume of oxygen, 10% by volume of steam and 73% by volume of nitrogen was passed through the catalyst layer at a contact time of 4.5 seconds with the temperature of the heat medium bath being kept at 325° C. The reaction products were analyzed; as a result, the conversion of isobutylene was 95.5%, the selectivity of methacrolein was 87.7% and the selectivity of methacrylic acid was 5.3%. This reaction was conducted continuously in the same manner as in Example 1. When the reaction was continued until the temperature of the heat medium bath became 340° C., the time period of continuous operation was 12,000 hours. At that time, the conversion of isobutylene was 95.7%, the selectivity of methacrolein was 87.7% and the selectivity of methacrylic acid was 5.3%.

The reaction was stopped; air was passed through the catalyst layer at a contact time of 4.0 seconds; the temperature of the heat medium bath was increased to 380° C. and kept at the same temperature for 24 hours; thereby, a first catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of isobutylene was 95.1%, the selectivity of methacrolein was 87.7% and the selectivity of methacrylic acid was 5.3%. This reaction was conducted continuously in the same manner as above. When the reaction was continued until the temperature of the heat medium bath became 340° C., the time period of continuous operation after the activation treatment was 6,000 hours. At that time, the conversion of isobutylene was 95.7%, the selectivity of methacrolein was 87.5% and the selectivity of methacrylic acid was 5.3%.

The reaction was stopped again; air was passed through the catalyst layer at a contact time of 4.0 seconds; the temperature of the heat medium bath was increased to 380° C. and kept at the same temperature for 24 hours; thereby, a second catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of isobutylene was 95.0%, the selectivity of methacrolein was 87.7% and the selectivity of methacrylic acid was 5.3%. This reaction was conducted continuously in the same manner as above. When the reaction was continued until the temperature of the heat medium bath became 340° C., the time period of continuous operation after the activation treatment was 4,800 hours. At that time, the conversion of isobutylene was 94.8%, the selectivity of methacrolein was 87.5% and the selectivity of methacrylic acid was 5.3%.

The reaction was stopped once again; air was passed through the catalyst layer at a contact time of 4.0 seconds; the temperature of the heat medium bath was increased to 380° C. and kept at the same temperature for 24 hours; thereby, a third catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of isobutylene was 95.0%, the selectivity of methacrolein was 87.7% and the selectivity of methacrylic acid was 5.3%. This reaction was conducted continuously in the same manner as above. When the reaction was continued until the temperature of the heat medium bath became 340° C., the time period of continuous operation after the activation treatment was 3,600 hours. At that time, the conversion of isobutylene was 94.2%, the selectivity of methacrolein was 87.5% and the selectivity of methacrylic acid was 5.3%.

Example 2

2,000 g of the catalyst obtained in Reference Example was packed in the same reaction tube as used in Reference Example. Then, a raw material mixed gas composed of 5% by volume of tertiary butanol, 12% by volume of oxygen, 10% by volume of steam and 73% by volume of nitrogen was passed through the catalyst layer at a contact time of 4.5 seconds with the temperature of the heat medium bath being kept at 325° C. The reaction products were analyzed; as a result, the conversion of tertiary butanol was 100%, the selectivity of methacrolein was 83.4% and the selectivity of methacrylic acid was 5.1%. This reaction was conducted continuously in the same manner as in Example 1. That is, the temperature of the heat medium bath was controlled when the conversion changed owing to the change in catalytic activity, whereby the conversion was kept substantially constant. It was actually conducted by assuming that tertiary butanol, when contacted with the catalyst, is totally composed into isobutylene and water rapidly, measuring the concentration of isobutylene in the gas after reaction to determine the conversion of isobutylene, and keeping the conversion substantially constant. When the reaction was continued until the temperature of the heat medium bath became 330° C., the time period of continuous operation was 9,600 hours. At that time, the conversion of tertiary butanol was 100%, the selectivity of methacrolein was 83.2% and the selectivity of methacrylic acid was 5.1%.

The reaction was stopped; a mixed gas composed of 15% by volume of oxygen and 85% by weight of nitrogen, instead of the raw material mixed gas, was passed through the catalyst layer at a contact time of 4.0 seconds; the temperature of the heat medium bath was increased to 380° C. and kept at the same temperature for 24 hours; thereby, a first catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of tertiary butanol was 100%, the selectivity of methacrolein was 83.4% and the selectivity of methacrylic acid was 5.1%. This reaction was conducted continuously in the same manner as above. When the reaction was continued until the temperature of the heat medium bath became 330° C., the time period of continuous operation after the activation treatment was 8,400 hours. At that time, the conversion of tertiary butanol was 100%, the selectivity of methacrolein was 83.2% and the selectivity of methacrylic acid was 5.1%.

The reaction was stopped again; a mixed gas composed of 15% by volume of oxygen and 85% by weight of nitrogen, instead of the raw material mixed gas, was passed through the catalyst layer at a contact time of 4.0 seconds; the temperature of the heat medium bath was increased to 380° C. and kept at the same temperature for 24 hours; thereby, a second catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of tertiary butanol was 100%, the selectivity of methacrolein was 83.3% and the selectivity of methacrylic acid was 5.1%. This reaction was conducted continuously in the same manner as above. When the reaction was continued until the temperature of the heat medium bath became 330° C., the time period of continuous operation after the activation treatment was 8,400 hours. At that time, the conversion of tertiary butanol was 100%, the selectivity of methacrolein was 83.2% and the selectivity of methacrylic acid was 5.1%.

The reaction was stopped once again; a mixed gas composed of 15% by volume of oxygen and 85% by weight of nitrogen, instead of the raw material mixed gas, was passed through the catalyst layer at a contact time of 4.0 seconds; the temperature of the heat medium bath was increased to 380° C. and kept at the same temperature for 24 hours; thereby, a third catalyst activation treatment was conducted. Thereafter, the heat medium bath was cooled to 325° C. and the same raw material mixed gas as used above was passed through the catalyst layer at a contact time of 4.5 seconds to restart the reaction. The reaction products were analyzed; as a result, the conversion of tertiary butanol was 100%, the selectivity of methacrolein was 83.3% and the selectivity of methacrylic acid was 5.1%. This reaction was conducted continuously in the same manner as above. When the reaction was continued until the temperature of the heat medium bath became 330° C., the time period of continuous operation after the activation treatment was 8,400 hours. At that time, the conversion of tertiary butanol was 100%, the selectivity of methacrolein was 83.2% and the selectivity of methacrylic acid was 5.1%.

Industrial Applicability

In the present process for producing methacrolein and methacrylic acid, the catalyst can be used for a significantly long period of time.

What is claimed is:

1. A process for producing methacrolein and methacrylic acid by catalytically oxidizing isobutylene or tertiary butanol in the presence of a catalyst comprising a compound oxide containing molybdenum, bismuth and iron as essential components, wherein a catalytic oxidation reaction is started at a temperature of (T–3)° C. or lower wherein T° C. is defined as a boundary temperature of activation energy of a reaction for obtaining methacrolein and methacrylic acid from isobutylene using said catalyst, the reaction is continued while a reaction temperature is increased as an activity of the catalyst decreases, and an activation treatment is conducted for the catalyst at least once before the reaction temperature exceeds the boundary temperature of activation energy.

2. The process according to claim 1, wherein the activation treatment comprises keeping said catalyst at a temperature ranging from 300° to less than 550° C. and contacting said catalyst with air for at least one hour.

3. The process according to claim 1, wherein the activation treatment comprises taking out said catalyst from a reactor in which the catalytic oxidation reaction is carried out.

4. The process according to claim 1, wherein the activation treatment is carried out on the catalyst, said catalyst being packed in a reactor in which the catalytic oxidation reaction is carried out.

5. The process according to claim 1, wherein said catalyst comprises

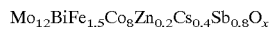

wherein x is the atomic ratio of oxygen satisfying the valencies of the elements in said catalyst other than oxygen.

6. The process according to claim 1, comprising oxidizing isobutylene.

7. The process according to claim 1, comprising oxidizing tertiary butanol.

* * * * *